(12) United States Patent
Kraus (10) Patent No.: US 7,827,845 B2
(45) Date of Patent: Nov. 9, 2010

(54) METHOD AND KIT FOR MAINTAINING A STERILE ENVIRONMENT DURING CALIBRATION OF A MEDICAL DEVICE

(75) Inventor: Robert G. Kraus, Attleboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 662 days.

(21) Appl. No.: 11/764,293

(22) Filed: Jun. 18, 2007

(65) Prior Publication Data
US 2008/0307854 A1 Dec. 18, 2008

(51) Int. Cl.
*G01L 27/00* (2006.01)
(52) U.S. Cl. ...................................... 73/1.59
(58) Field of Classification Search ................ None
See application file for complete search history.

(56) References Cited

U.S. PATENT DOCUMENTS

| | | | |
|---|---|---|---|
| 3,886,948 A | | 6/1975 | Hakim |
| 4,331,156 A | * | 5/1982 | Apple et al. ............... 600/501 |
| 4,332,255 A | | 6/1982 | Hakim et al. |
| 4,387,715 A | | 6/1983 | Hakim et al. |
| 4,475,555 A | * | 10/1984 | Linder ....................... 600/483 |
| 4,551,128 A | | 11/1985 | Hakim et al. |
| 4,568,330 A | | 2/1986 | Kujawski et al. |
| 4,595,390 A | | 6/1986 | Hakim et al. |
| 4,615,691 A | | 10/1986 | Hakim et al. |
| 4,737,020 A | | 4/1988 | Parker |
| 4,772,257 A | | 9/1988 | Hakim et al. |
| 4,838,664 A | | 6/1989 | Graham |
| 4,941,308 A | | 7/1990 | Grabenkort et al. |
| 4,945,919 A | | 8/1990 | Hattori |
| 5,321,989 A | | 6/1994 | Zimmer et al. |
| 5,329,804 A | | 7/1994 | Germany et al. |

(Continued)

FOREIGN PATENT DOCUMENTS

EP 0476948 3/1992

(Continued)

OTHER PUBLICATIONS

Microsensor Instruction for Use; May 28, 2002.*

(Continued)

*Primary Examiner*—Robert R Raevis
(74) *Attorney, Agent, or Firm*—Nutter McClennen & Fish LLP (57) ABSTRACT

A method for maintaining a medical device in a sterile atmosphere at a desired temperature during a calibration step is provided. The method includes packaging a medical device and temperature indicator in a sterile container such that the indicator is visible to a user. Next, heat can be applied to the container in order to stabilize the temperature of the container (as indicated by the encased temperature indicator) at room temperature. Once at room temperature, the device can be calibrated while remaining in the sterile atmosphere. A kit including such a container and a set of instructions is also provided. Like above, the container of the kit can include a sterile medical device and temperature indicator such that the device can be maintained in a sterile environment during calibration and/or zeroing. As such, the method and kit allow for increased precision and safety in performing medical procedures.

18 Claims, 7 Drawing Sheets

U.S. PATENT DOCUMENTS

| | | | |
|---|---|---|---|
| 5,431,057 A | 7/1995 | Zimmer et al. | |
| 5,486,659 A * | 1/1996 | Rosenbush | 181/131 |
| 5,928,182 A | 7/1999 | Kraus et al. | |
| 6,360,888 B1 | 3/2002 | McIvor et al. | |
| 6,560,471 B1 * | 5/2003 | Heller et al. | 600/347 |
| 6,582,653 B1 * | 6/2003 | Warburton-Pitt | 422/26 |
| 2002/0034212 A1 * | 3/2002 | Faries et al. | 374/150 |
| 2006/0211946 A1 | 9/2006 | Mauge | |

FOREIGN PATENT DOCUMENTS

| | | |
|---|---|---|
| EP | 1312302 | 5/2003 |
| WO | WO2008/001091 | 1/2008 |

OTHER PUBLICATIONS

European Search Report, from corresponding EP Appl. No. 08252079.2, dated Jul. 6, 2010.

* cited by examiner

METHOD AND KIT FOR MAINTAINING A STERILE ENVIRONMENT DURING CALIBRATION OF A MEDICAL DEVICE

FIELD OF THE INVENTION

The present invention relates to a method and kit capable of maintaining a sterile environment during calibration of a medical device, in particular during a temperature-specific calibration of an implantable sensor.

BACKGROUND OF THE INVENTION

Medical procedures typically require the use of sterile medical devices. Some such devices need to be calibrated at a specific temperature prior to use. However, bringing the device to the desired temperature and/or calibrating the device can contaminate the device, thereby potentially adding complications to the procedure by requiring further sterilization steps before use.

Various medical sensors typically face such difficulties. Prior to use, these sensors must be calibrated and/or zeroed at a desired temperature (e.g., body temperature). One common method for performing the calibration includes warming sterile water or saline to a desired temperature in order to mimic body conditions while maintaining a sterile environment. In such a method, the sterile sensor can be removed from a packaging and placed into the sterile water or saline. Next, a non-sterile calibration device can be brought into communication with the sensor in order to perform the desired calibration. Such a procedure is deficient in many regards. First, the presence of the non-sterile calibration device risks contamination of the sensor. Next, due to such risk, the procedure can limit the proximity of the calibration device to the sterile sensor thereby potentially resulting in an inaccurate calibration. As such, the above-described calibration procedure is inefficient and error-prone.

For some sensor-based devices, the device is best calibrated at an exact temperature immediately prior to use. For example, certain implantable intra-cranial pressure sensors need to be zeroed exactly at body temperature immediately prior to implantation. Such invasive procedures require accurate calibration steps while maintaining sterility in order to enhance patient safety and increase the success rate of the procedure.

SUMMARY OF THE INVENTION

The presently disclosed embodiments provide methods and kits for maintaining a medical device in a sterile atmosphere during a calibration and/or zeroing procedure. More specifically, the presently disclosed embodiments allow for a user to accurately bring the medical device to an extremely specific desired temperature (e.g., body temperature) and perform a required calibration and/or zeroing step without removing the device from the sterile environment. As will be shown, the presently disclosed embodiments allow for the device to remain within the container during the calibration step and therefore right up to the point of use (e.g., implantation). Therefore, the presently disclosed method and kit allow for increased precision and safety in performing medical procedures. Various aspects of the invention are summarized below.

In one aspect, the invention provides a method for calibrating a medical device at an extremely specific temperature while maintaining the sterility of the device. The method can include packaging a temperature indicator adjacent to a medical device within a sterile container so that the indicator can accurately determine and indicate the current temperature of the medical device. Further, the temperature indicator can be positioned within the sterile container so as to remain visible to a user (i.e., through a clear portion of the container). Additionally, the temperature indicator can include an adhesive layer capable of securing the indicator at the desired position within the sterile container.

Next, the method can include applying and/or removing heat to the container so as to bring the medical device to the desired temperature. The temperature indicator can indicate a temperature change and, more specifically, indicate to the user (for example, via a visible color change) when the medical device has stabilized at the desired temperature. In an exemplary embodiment, the temperature indicator can utilize microencapsulated liquid crystal technology thereby allowing for a visible color change indicative of a temperature change in the range of about 0.5° C. to about 2.0° C.

Once the temperature of the medical device has stabilized at the desired temperature (as indicated by the visible temperature indicator), a user can calibrate and/or zero the medical device. Following calibration, the method can further include removing the sterile medical device from the container, and performing a desired procedure with the medical device (e.g., implanting the medical device in a patient).

The medical device can be any type of device which should be maintained in a sterile environment prior to use and, more specifically, maintained in a sterile condition during a calibration step performed at a desired temperature. For example, the device can be a sensor such as an implantable pressure sensor, a temperature sensor, an oxygen sensor, a pH sensor, etc. More specifically, the device can be an implantable pressure sensor capable of measuring an intra-ventricular pressure wherein the sensor is calibrated at body temperature immediately prior to use (i.e., implantation on or within a patient's skull).

In another aspect of the invention, a kit is provided which can include a sterile container (e.g., a blister packaging) housing a medical device and a temperature indicator. As indicated above, the container can maintain the medical device and temperature indicator in a sterile condition. Further, the temperature indicator can be positioned adjacent to the medical device so as to be capable of accurately indicating the current temperature of the medical device. Also, the temperature indicator can be positioned relative to the container so as to be visible to a user through a clear portion of the sterile container. Like above, the temperature indicator can be capable of indicating when the temperature indicator is at the desired temperature thereby providing an accurate indication of when the medical device is at the desired temperature and therefore ready for calibration. In addition to the medical device and temperature indicator, the kit can include instructions on how to use (e.g., steps to follow when calibrating the particular medical device).

These and other aspects of the presently disclosed embodiments will be discussed in detail below.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The presently disclosed embodiments provide a method and kit capable of maintaining a medical device in a sterile environment during a calibration step. More specifically, the method can accurately determine the temperature of the medical device while the medical device remains disposed in a sterile container so as to allow for the device to be calibrated at a desired temperature (e.g., body temperature) while the device remains in the container. The temperature of the device can be accurately determined by a temperature indicator also disposed within the sterile container, and positioned adjacent to (e.g., above, near or underneath) the device so as to be capable of accurately determining the temperature of the medical device. Also, the temperature indicator can be positioned relative to the container such that the indicator is visible to a user through a clear portion of the container.

Figure 1:
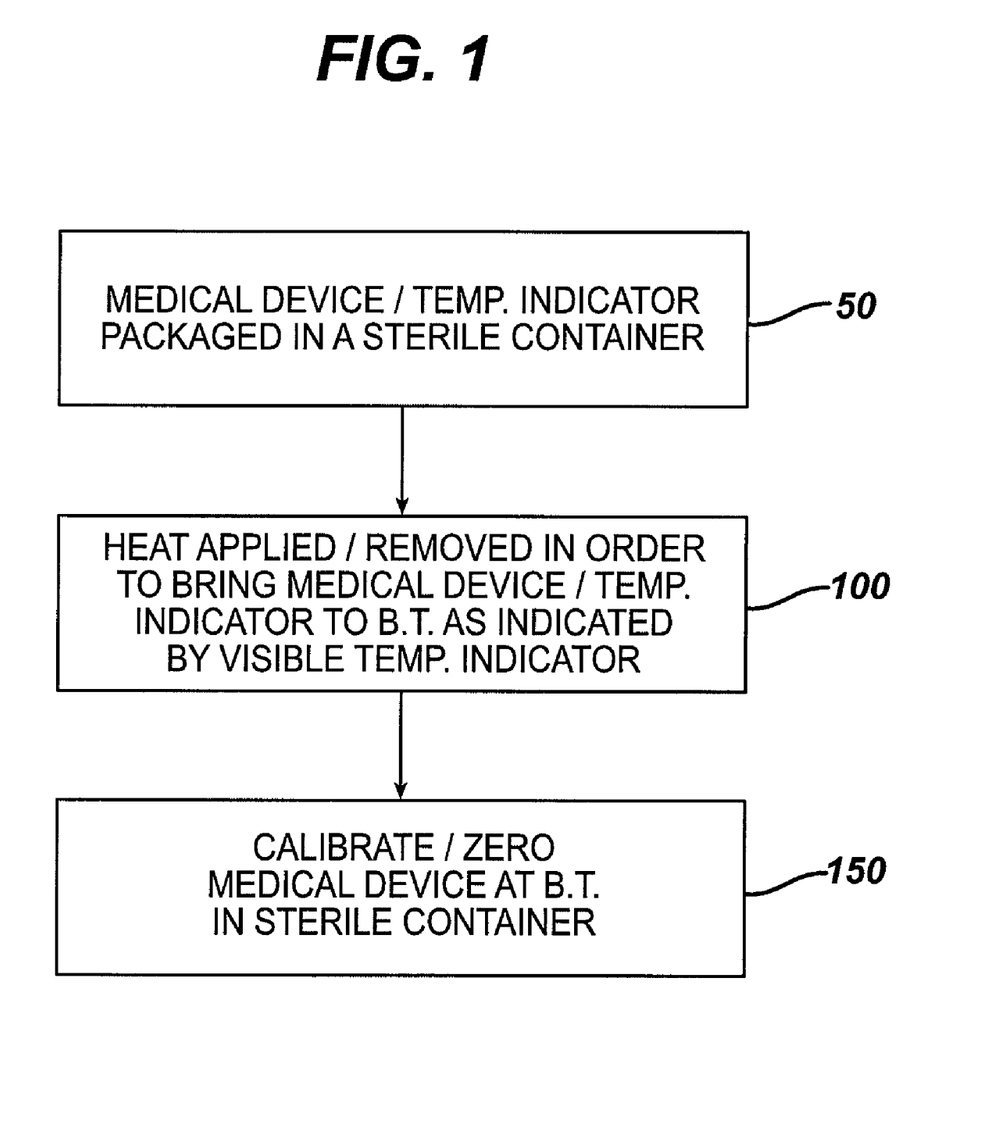
FIG. 1 is a diagrammatic overview of an exemplary embodiment of the presently disclosed method.

FIG. 1 provides a general overview of an exemplary embodiment of steps included in the presently disclosed method. As shown, the method can generally be represented by three steps. Initially, the method can include packaging a medical device and temperature indicator within a sterile container (Step 50). Next, heat can be applied (or removed, if necessary) in order to place the contents of the container (i.e., the medical device and the temperature indicator) at the desired calibration temperature (such as body temperature, "B.T.") (Step 100). Once at the desired temperature, the device can be calibrated and/or zeroed while the device remains in a sterile environment (Step 150). Steps 50, 100, and 150 will now be discussed in detail.

As stated, the initial step (Step 50) includes packaging a medical device and a temperature indicator within a sterile container. In this exemplary embodiment, the medical device contains a temperature-sensitive sensor. Typically, such medical devices are required to be calibrated at a specific temperature immediately prior to use. Furthermore, the sterility of such devices must be maintained up to and during such calibration steps. These sensors can include pressure sensors, temperature sensors, pH sensors, oxygen sensors, or any other type of sensors.

Figure 2:
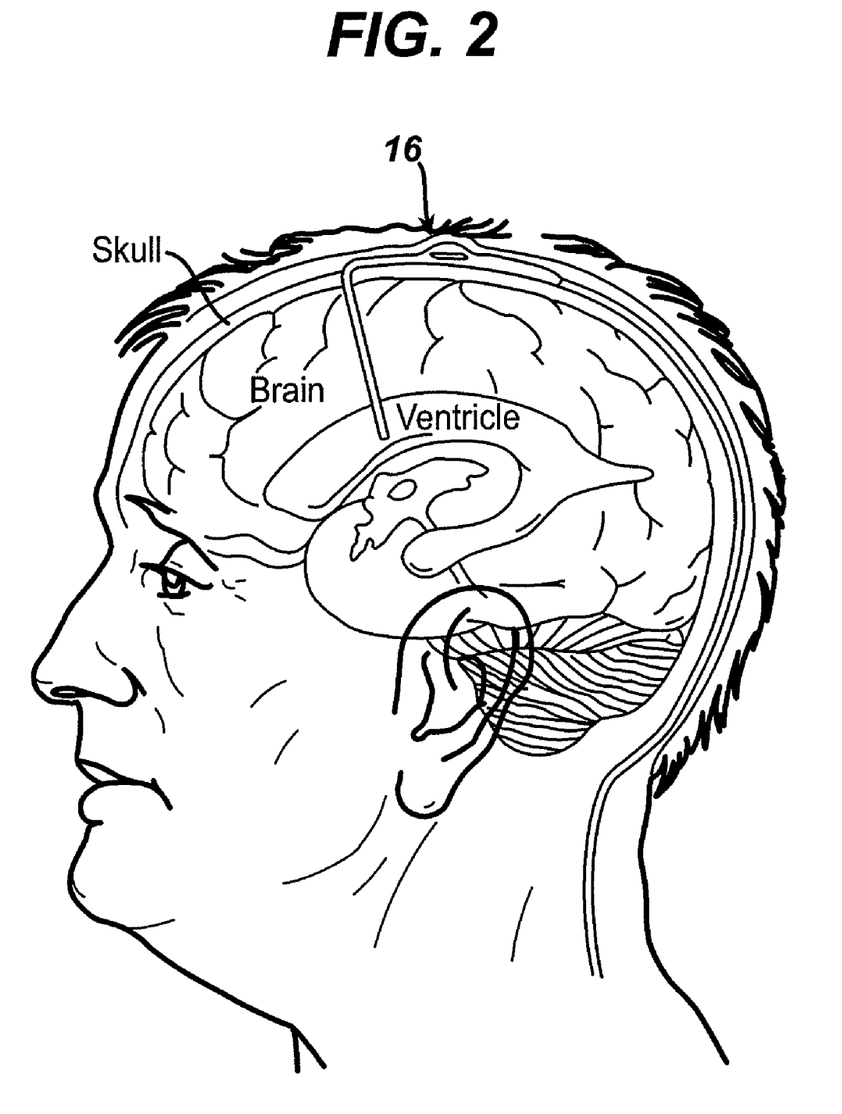
FIG. 2 is a representation of an implantable pressure sensor in communication with a patient's brain.

In an exemplary embodiment, the device can be one of the embodiments of implantable shunt devices having pressure sensors as disclosed in assignee's co-pending U.S. patent applicant Ser. No. 10/907,665, filed on Apr. 11, 2005, entitled "Pressure Sensing Devices," the entirety of which is incorporated herein by reference. As shown FIG. 2, such a device 16 can be placed in communication with a patient's ventricle so as to measure an intra-ventricular pressure. Due to the invasive nature of such devices, maintaining the sterility of the device 16 up to the point of implantation is important. Furthermore, in order to accurately utilize the device 16, the implantable pressure device 16, and in particular its pressure sensor, needs to be zeroed at body temperature immediately prior to implantation.

Figure 3A:
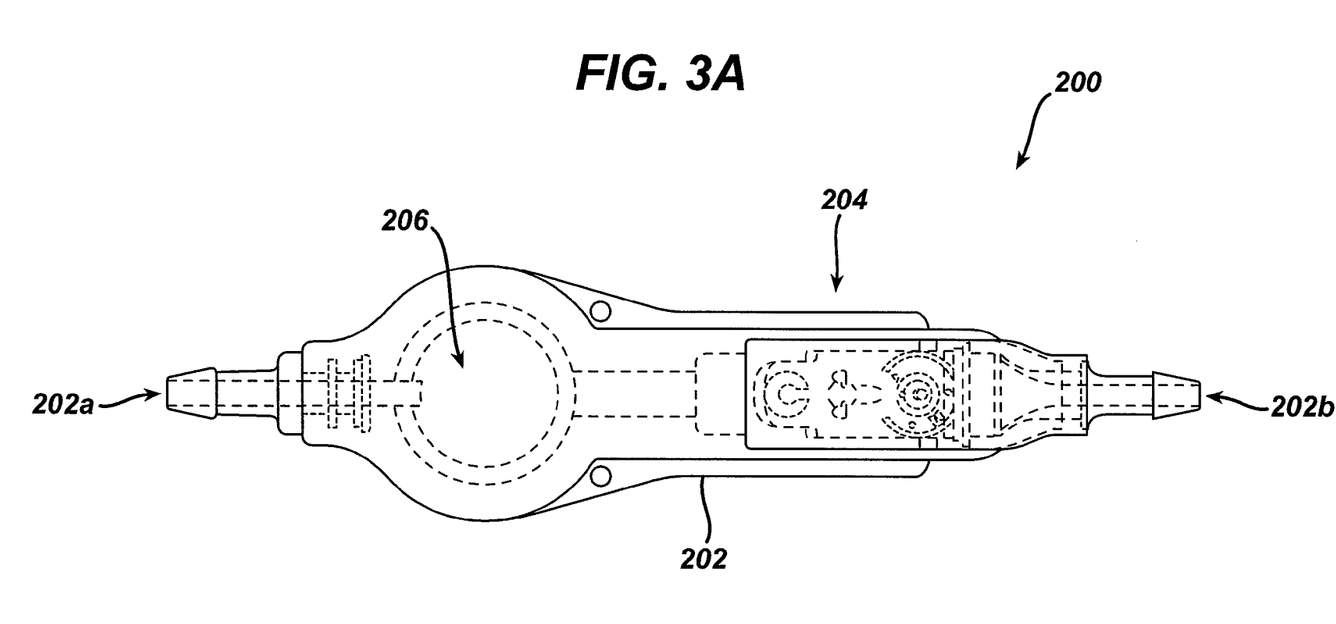
FIG. 3A is a top view of an implantable device having a pressure sensor capable of being utilized with an embodiment of the presently disclosed method and/or kit.
Figure 3B:
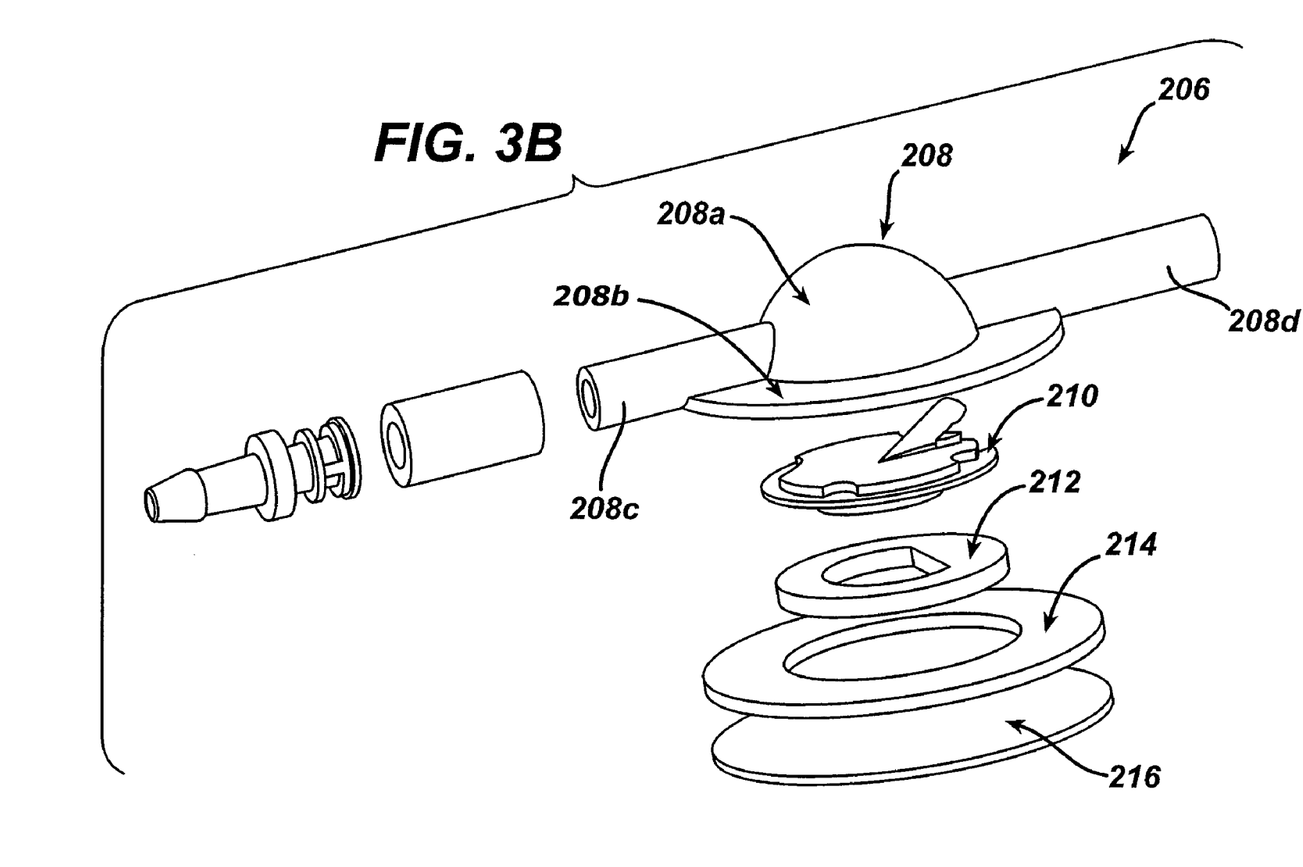
FIG. 3B is an exploded view of the implantable device of FIG. 3A.

FIGS. 3A and 3B provide an exemplary embodiment of such an implantable device capable of being utilized with the presently disclosed kit or method. As such, a pressure sensor assembly 206 is shown that can be disposed within a valve housing of an implantable shunt or valve 200 that can be used to control fluid flow. The exemplary valve 200 can be used alone or in combination with a pressure sensor assembly that is disposed in the distal portion of a ventricular catheter, and/or other pressure sensor assemblies disposed upstream or downstream of the valve 200.

While the implantable valve 200 can have virtually any configuration, and a variety of implantable valves or reservoirs known in the art can be used, FIG. 3A illustrates an implantable valve 200 having valve housing 202 with an inlet 202a and an outlet 202b. The valve housing 202 can contain a valve mechanism 204 for controlling the flow of fluid from the inlet 202a to the outlet 202b, and a pressure sensor assembly 206 for measuring a pressure of the fluid flowing through the valve 200, as will be described in more detail with respect to FIG. 3B. While the valve mechanism 204 and pressure sensor assembly 206 of the valve 200 are shown in-line with one another and with the inlet 202a and outlet 202b, and the pressure sensor assembly 206 is positioned upstream of the valve 200, the valve 200 can have a variety of other configurations and the valve mechanism 204, pressure sensor assembly 206, inlet 202a, and outlet 202b can be positioned at various locations relative to one another. For example, the inlet 202a can extend at a right angle with respect to the pressure sensor assembly 206 such that the inlet 202a extends in a direction substantially transverse to a longitudinal axis of the valve 200. The valve mechanism 204 can also have a variety of configurations. By way of non-limiting example, exemplary valves are described in U.S. Pat. Nos. 3,886,948, 4,332,255, 4,387,715, 4,551,128, 4,595,390, 4,615,691, 4,772,257, and 5,928,182, all of which are hereby incorporated by reference.

An exemplary pressure sensor assembly 206 is shown in more detail in FIG. 3B, can include a housing or reservoir 208, a sensor 212, and a backing 216. The illustrated pressure sensor assembly 206 also includes a needle guard 210 and a washer 214, as will be discussed in more detail below.

The sensor housing 208 can have a variety of shapes and sizes, but in the illustrated exemplary embodiment the sensor housing 208 has a generally hemi-spherical or domed portion 208a that defines a pumping reservoir therein. The sensor housing 208 can also include an inlet tube 208c that couples to the inlet 202a of the valve 200, and an outlet tube 208d that couples to the outlet 202b of the valve 200. When the sensor housing 208 is mated to the backing 216, the reservoir chamber defined by the housing 202 is sealed, thereby allowing fluid to flow from the inlet 202a of the valve 200, through the sensor housing 208, through the valve mechanism 204, and out the outlet 202b in the valve 200. The sensor housing 208 can also include a flange 208b formed around a base of the domed portion 208a to allow the device to be secured to tissue. For example, the flange 208b can include one or more suture holes formed therein for receiving suture to attach the flange 208b to tissue.

As mentioned above, the sensor housing 206 can include a sensor 212 disposed therein. The sensor 212 can be formed on a microchip which can be coupled to an antenna for communicating a sensed pressure to an external device. The antenna can have a substantially circular shape, and the microchip sensor can be coupled to the antenna. The antenna can take various forms such as, for example, a gold microcoil. The sensor 212 can also include a fluid-impermeable coating disposed there around, as previously described, to protect the sensor from fluid flowing through the sensor housing 208. The size will vary depending on the valve 200, but in one exemplary embodiment the microchip sensor 212 has a size that is in the range of about 1 mm to 3 mm, and more preferably that is about 2.5 mm$^2$. As previously indicated, exemplary embodiments of a pressure sensor and antenna are described in more detail in U.S. Pat. No. 5,321,989, U.S. Pat. No. 5,431,057, and EP Patent No. 1 312 302.

In use, the sensor 212, which is disposed within the sensor housing 208, is adapted to measure the pressure of fluid flowing through the sensor housing 208. In particular, the inlet 202a of the valve 200 can be coupled to a ventricular catheter for receiving fluid flow from the ventricles, and the outlet 202b can be coupled to a drainage catheter. As the fluid enters the sensor housing 208, the pressure of the fluid will apply a force to active sensor membranes formed on the sensor 212, thereby allowing the fluid pressure to be measured. The sensed pressure can be communicated, via the antenna, to an external reading device.

As previously mentioned, and as further shown in FIG. 3B, the sensor assembly 206 can also include a washer 214. The washer 214 can be provided to seat the sensor 212, such that the washer 214 and sensor 212 are positioned against the backing 216. The washer 214 can also be configured such that the sensor 212 is sub-flush with the washer 214. Such a configuration may protect the sensor 212 from potential damage when the domed portion 208a of the housing 208 is depressed to pump fluid through the housing 208, or to otherwise test the valve or clear the valve from debris, etc.

As further shown in FIG. 3B, the sensor assembly 206 can also include a needle guard 210 for protecting the sensor 212. In particular, the needle guard 210 can protect the sensor 212 from coming into contact with the domed portion 208a of the housing 208 when the domed portion 208a is depressed, as the needle guard 210 can be positioned between the sensor 212 and the domed portion 208a. The needle guard 210 can also be provided to protect the sensor from a needle being inserted through the domed portion 208a of the sensor housing 208, thereby preventing potential damage to the sensor 212. A needle may be used to deliver or withdraw fluid from the sensor housing 208. While the shape of the needle guard 210 can vary depending on the shape of the sensor assembly 206, in an exemplary embodiment, as shown, the needle guard 210 has a substantially planar, circular shape and it is adapted to be disposed between the domed portion 208a of the housing 208 and the sensor 212. The needle guard 210 can, however, include an opening formed therein and positioned adjacent to the microchip sensor 212 to allow fluid flowing through the sensor housing 208 to come into contact with the sensor 212. In an exemplary embodiment, a flange or protective member is disposed over the opening, without blocking the opening from fluid flow, to prevent a user from accidentally inserted a needle through the opening. A person skilled in the art will appreciate that a variety of other techniques can be used to protect the sensor 212.

An additional description and further embodiments of such implantable pressure sensors can be found in assignee's incorporated application, U.S. patent application Ser. No. 10/907,665.

Figure 4:
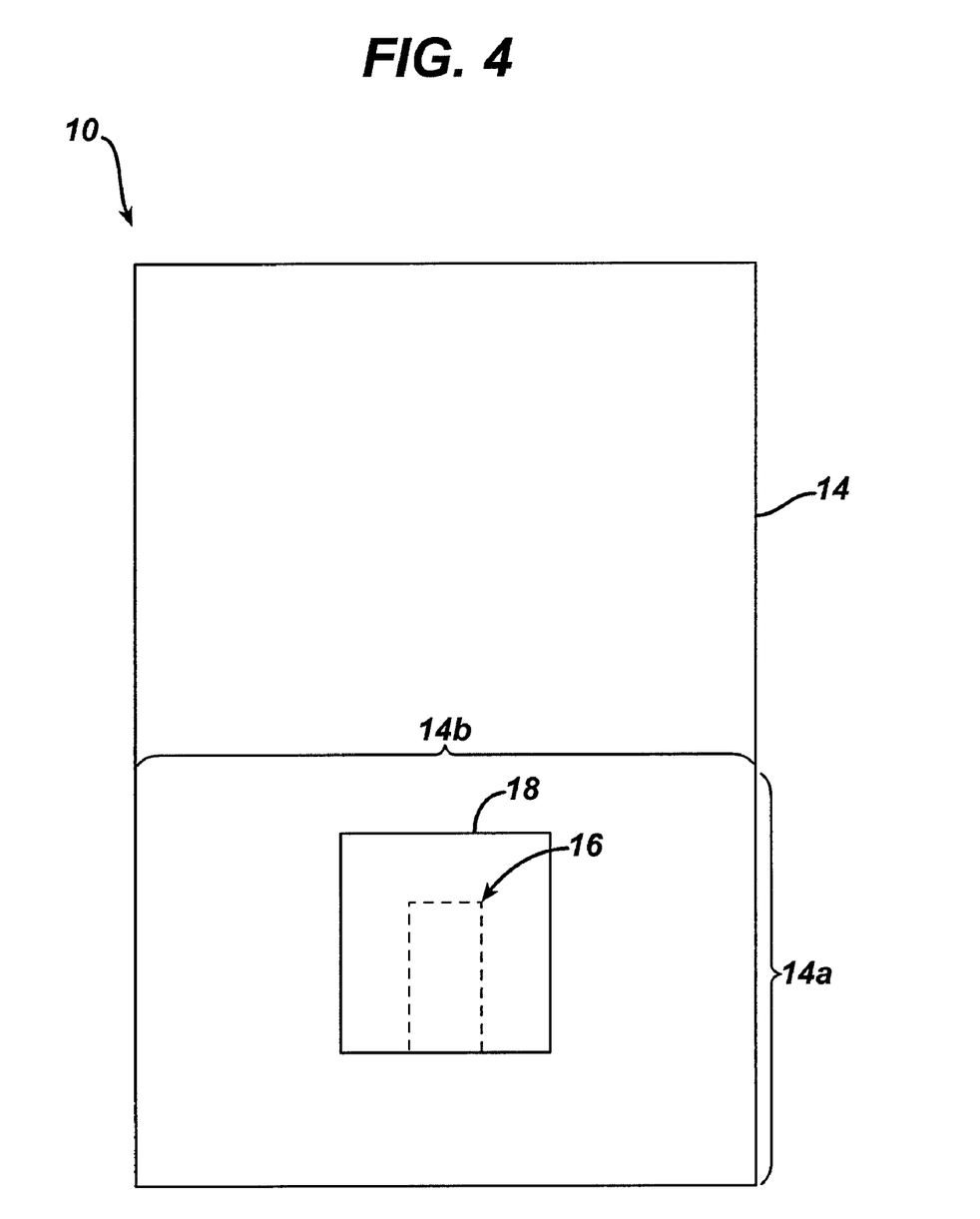
FIG. 4 is a front view of an exemplary embodiment of a blister package capable of maintaining a medical device in a sterile environment.

The presently disclosed method further includes, as shown diagrammatically in FIG. 4, packaging a temperature indicator 18 within the container 12 so that the indicator 18 and medical device 16 are maintained in a sterile atmosphere. Additionally, the temperature indicator 18 can be positioned relative to the medical device 16 such that the reading of the temperature indicator 18 can provide an accurate reading as to the temperature of the medical device 16. As such, the temperature indicator 18 can be placed above, adjacent to, near, beneath, etc. of the medical device such that the temperature indicator 18 provides an accurate reading as to the temperature of the medical device 16. Where it is a sensor on the medical device 16 that will be calibrated at temperature, the temperature indicator 18 should be placed so as to provide an accurate reading of the temperature of that part of the device 16.

Additionally, the components (e.g., the temperature indicator 18 and medical device 16) can be packaged such that the temperature indicator 18 is visible to a user prior to removing the medical device 16 from the sterile environment. As will be discussed, such packaging allows for a user to visualize a color change of the indicator 18 which indicates a temperature change and ultimately indicates when the temperature of the indicator 18, and thereby the medical device 16, has stabilized at the desired temperature (i.e., the calibration temperature).

In the embodiment of FIG. 4, a length 14a and a width 14b of the container 14 includes a transparent material (e.g. a polymer or mixture of polymers) such that a user can visualize the temperature indicator 18 while the indicator 18 remains in the sterile environment. As shown, the medical device 16 (as indicated by dashed lines) can be positioned beneath the temperature indicator 18 such that the indicator 18 can accurately determine and indicate the temperature of the medical device. In an exemplary embodiment, the container 14 can include a blister packaging. Furthermore, the sterile container 14 can be disposed within an outer container 12 (shown in FIG. 5) capable of preventing damage to the device 16 during shipping and/or storing of the kit 10. As will be appreciated by those skilled in the art, various configurations of containers 12, 14 are within the spirit and scope of the present invention.

Figure 5:
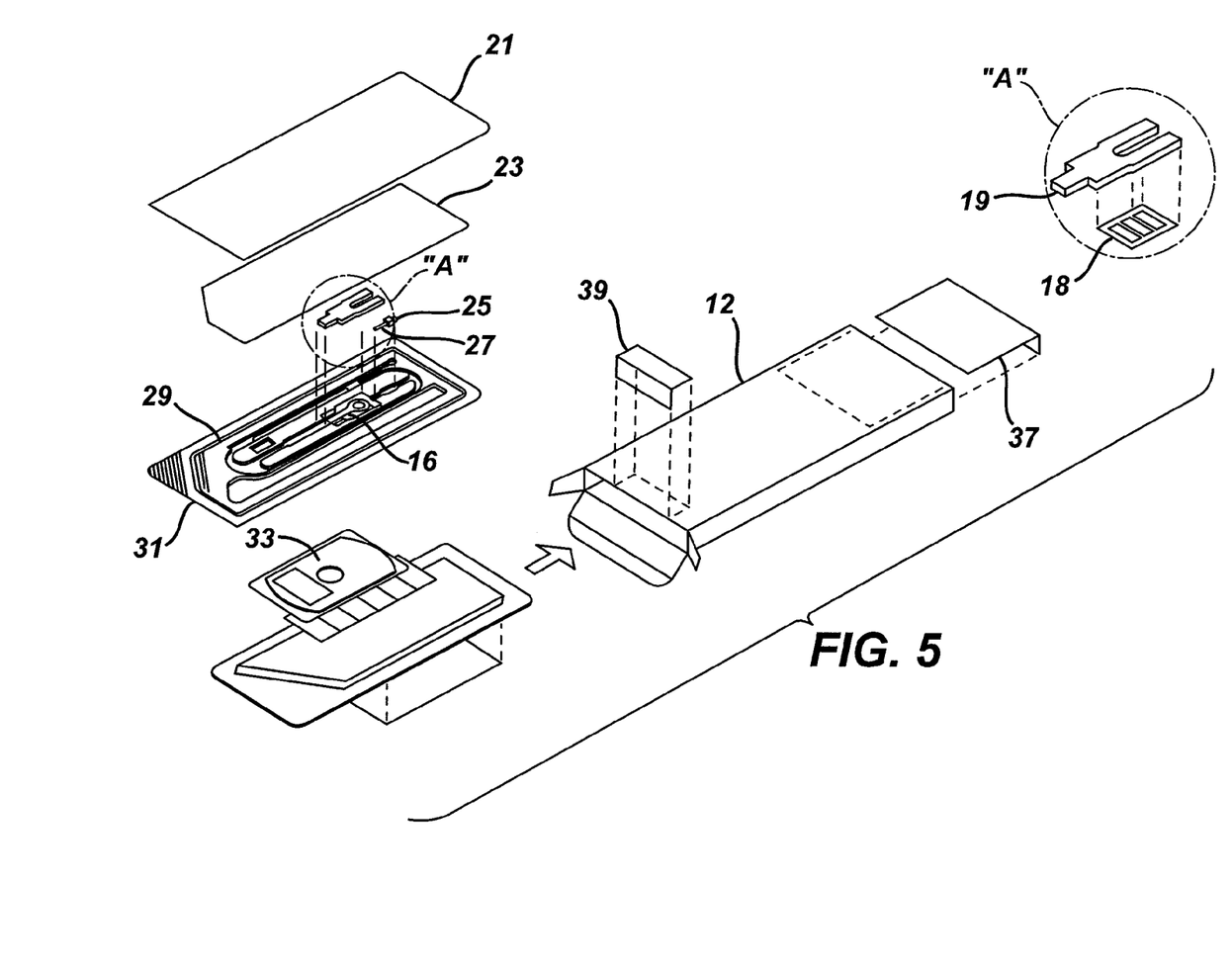
FIG. 5 is an exploded view of the container of FIG. 4 showing various components capable of being housed within the container.

As illustrated in the exploded view of FIG. 5, various components can be included within the outer container 12 so as to maximize the sterility of the medical device 16, as well as maximize the accuracy of the temperature indicator 18. As shown, the medical device 16 can be positioned so as to be housed in a multi-layered 21, 23, 29, 31 blister packaging. Additionally, the temperature indicator 18 can be adhered (e.g., via an adhesive) to one side of a foam (or similar type material) retainer 19 such that the retainer 19 can be positioned immediately above the device 16 thereby allowing the indicator 18 to accurately determine the temperature of the medical device 16. Furthermore, various identification elements (e.g., radiopaque tube 27 and/or sensor identification 25) can be housed within the sterile container 14.

Various other components can also be included within the outer container 12. For example, various patient/user information, instructions for use, etc. can be included in the container 12. As shown, a CD/DVD 33 having such instructions can be included in the container 12. Prior to shipping and/or storage, appropriate labeling 37 can be applied to the container 12. As will be apparent to one skilled in the art, various components can be added or removed from the embodiment described above while remaining within the spirit and scope of the present invention.

Referring now to the temperature indicator 18, the indicator 18 can be any device capable of accurately determining and providing a visible indication of a temperature change. For example, the temperature indicator 18 can provide a color change or a numerical change in response to a temperature change. In one embodiment, the temperature indicator 18 can detect and indicate (e.g., by color change) a change in temperature in the range of about 0.5° C. to about 2.0° C. In an exemplary embodiment, the temperature indicator 18 can detect and indicate a change in temperature of about 0.5° C.

Figure 6:
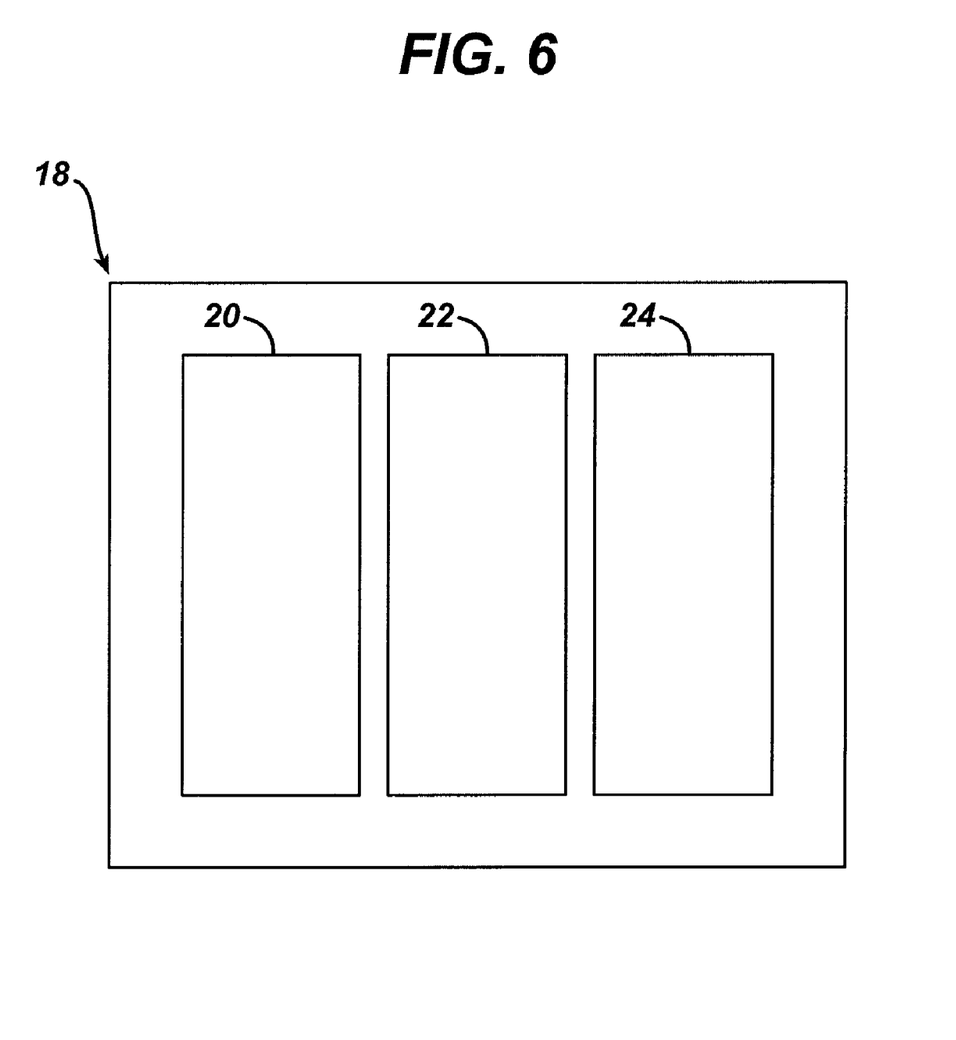
FIG. 6 is an exemplary embodiment of the presently disclosed temperature indicator.

FIG. 6 provides an exemplary embodiment of a temperature indicator 18 capable of being utilized in the presently disclosed method. As shown, the temperature indicator 18 can include a number of segments 20, 22, 24 wherein each segment is capable of responding (i.e., illuminating) to a particular temperature. In an exemplary embodiment, the segments 20, 22, 24 are capable of responding to three distinct temperatures respectively wherein temperature 1 is different from temperature 2 by about 0.5° C. to about 1.5° C., and temperature 2 is different from temperature 3 by about 0.5° C. to about 1.5° C. In an exemplary embodiment, the first segment 20 turns a color (e.g., green) to indicate a temperature of about 37° C. while the remaining segments 22, 24 remain black; next, the second segment 22 turns the color (can be green or a different color) to indicate a temperature of about 38° C. while the remaining segments 20, 24 remain (or return to) black. Finally, the third segment 24 can be adapted to turn color (green or another color) to indicate a temperature of about 39° C. while the remaining segments 20, 22 remain (or return to) black. As such, in this example, the temperature indicator 18 can differentiate between 37° C., 38° C., and 39° C. and thereby allow for the medical device 16 to be accurately calibrated and/or zeroed at the desired temperature (for example, 37° C. as opposed to 38° C.). Those skilled in the art will appreciate that the temperature indicator 18 can include any number and any shape of segments and remain within the spirit and scope of the present invention. Further, as will be appreciated, these segments can be adapted to indicate any range of temperatures (for example, 20° C., 21° C., 22° C. as opposed to 37° C., 38° C., 39° C.). In an exemplary embodiment, the temperature indicator 18 is a microencapsulated liquid crystal temperature indicator available from American Thermal Instruments, Inc. of Beavercreek, Ohio.

The term liquid crystal is one of the names given to a state of matter intermediate between that of the conventional crystalline solid and isotropic liquid. Other names include mesophase and mesomorphic state. Liquid crystals possess the mechanical properties of liquids (i.e., flow) and the optical properties of solids (i.e., they are anisotropic). Liquid crystals also possess some unique properties of their own which form the basis for their practical applications.

Many different types of liquid crystals exist. One particularly useful class of liquid crystals has been known historically as cholesteric liquid crystals. These materials have the ability to selectively reflect light and the color of the reflected light can be made to change as the temperature changes. The normal color change sequence is from red to green to blue (through the visible spectrum) with increasing temperature within their color reflective temperature range. Because of their unique temperature-sensitive properties, the materials are also called thermochromic liquid crystals (TLC's). The rate of change from one reflected color to another as well as the specific temperatures at which certain color changes occur can also be accurately controlled.

A common method of producing such devices is to produce a coating (ink) containing preferably a microencapsulated Thermochomic Liquid Crystal (TLC) mixture and use a printing method to apply it to the supporting substrate. A black ink is then applied on top of the dry TLC coating and color change effects are viewed from the reverse (uncoated) side of the sheet. Liquid crystal thermometers/temperature indicators are usually comprised of a series of liquid crystal 'events', which change color in a sequence as the temperature changes. Behind or adjacent to each number (temperature) on the TLC thermometers is an 'active' area coated with a precisely calibrated TLC mixture designed to change color at the temperature in question.

As will be apparent to those of skill in the art, the medical device 16 and temperature indicator 18 can be packaged within the container 12 by a manufacturer following generally accepted packaging procedures designed to optimize and ensure a sterile condition within the container 12. Any such packaging process is clearly within the spirit and scope of the present invention.

Referring back to FIG. 1, following the initial step (Step 50), the method includes applying a heat (or removing heat, if necessary) in order to bring the temperature indicator 18, and therefore the medical device 16, to a desired temperature. (Step 100). As discussed above, the temperature indicator 18 can be positioned relative to the medical device 16 such that the temperature of the temperature indicator 18 is indicative of the temperature of the medical device 16. In an exemplary embodiment, heat is applied and/or withdrawn (as necessary) to the sterile inner container 14 until the temperature indicator 18 (as seen through the clear container 14) indicates that the temperature has stabilized at the calibration temperature. In an exemplary embodiment, the calibration temperature is body temperature.

Those skilled in the art will appreciate that any device and/or method capable of applying and/or withdrawing heat to the container 14 may be utilized by the presently disclosed method. More specifically, any heating unit capable of delivering an amount of heat to the container 14 such that the contents of the container 14 (i.e., the medical device 16 and temperature indicator 18) can be maintained at a constant temperature for a desired duration is within the spirit and scope of the present invention.

When the temperature indicator 18 shows that the temperature of the medical device 16 has stabilized at the calibration temperature, the device 16 can be calibrated and/or zeroed for use (Step 150). Various medical procedures require the medical device 16 to be calibrated and/or zeroed at a desired temperature prior to use in order to obtain an accurate and reliable reading. As such, in an exemplary embodiment, the device 16 is calibrated while the temperature indicator 18 indicates that the temperature of the medical device 16 is at body temperature (such as in the case of the implantable pressure sensors discussed above). Once calibrated, the method can further include removing the sterile medical device 16 from the sterile container 14, and utilizing the medical device 16 in the desired procedure.

Those skilled in the art will appreciate that the method can include various added, subtracted, and/or modified steps. Such methods are clearly within the spirit and scope of the present invention.

In addition to the method disclosed above, a kit 10 (see FIG. 4) is also provided wherein the kit 10 includes a container 12 capable of housing a medical device 16 and temperature indicator 18 in a sterile condition. In addition, the kit 10 can include instructions on how to calibrate and/or zero the medical device 16 at a certain temperature with the aid of the temperature indicator 18. Like the method described above, the kit 10 allows for the medical device 16 to be calibrated at a desired temperature while maintaining a sterile environment at all times.

Using the device 200 of FIGS. 3A and 3B and the packaging of FIG. 5 as an example, the device can be packaged with the foam insert 19 pressing the temperature indicator 18 up against the device, and in particular, in the vicinity of pressure sensor 212. The identifier 25 packaged with the device can indicate a unique pressure sensor 212 for which calibration coefficients and/or data is available from the time of manufacture. The package can be heated until the temperature indicator indicates that the device has reached body temperature, and a hand held programmer/communication device (not shown) can be used to read a signal from the device that is indicative of pressure. Given that the sensor is at body temperature and atmospheric pressure, this reading will represent a "zeroing" of this individual sensor for purposes of comparing later signals from the device that will be used after implantation to calculate the absolute intracranial pressure of the patient's cerebrospinal fluid.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for calibrating a medical device, comprising:
    packaging a temperature indicator adjacent to a medical device within a sterile container such that the temperature indicator can determine and indicate a current temperature of the medical device, the temperature indicator capable of being visualized by a user through a clear portion of the sterile container;
    applying a heat to the sterile container until the temperature indicator indicates a desired temperature; and
    calibrating the medical device at the desired temperature.

2. The method of claim 1, further comprising:
    removing the medical device from the container; and
    performing a desired procedure with the medical device.

3. The method of claim 2, wherein the medical device is a sensor.

4. The method of claim 3, wherein the sensor is selected from the group consisting of: a temperature sensor, an oxygen sensor, and a pH sensor.

5. The method of claim 1, wherein the medical device is an implantable pressure sensor capable of measuring an intra-ventricular pressure.

6. The method of claim 5, wherein the implantable pressure sensor is calibrated at body temperature immediately before implanting the sensor in a patient's skull.

7. The method of claim 6, wherein the temperature indicator is a microencapsulated liquid crystal temperature indicator.

8. The method of claim 7, wherein the temperature indicator can detect and indicate a temperature change of about 0.5° C.

9. The method of claim 8, wherein the temperature indicator includes an adhesive layer capable of securing the temperature indicator at a desired position.

10. A kit, comprising:
    a sterile container housing a medical device and a temperature indicator, the temperature indicator being positioned relative to the medical device such that the temperature indicator is capable of providing a visual indication of a present temperature of the medical device, the temperature indicator further being positioned within the sterile container such that the indicator is visible to a user through a clear portion of the sterile container.

11. The kit of claim 10, wherein the medical device is a sensor.

12. The kit of claim 11, wherein the sensor is selected from the group consisting of: a pressure sensor, a temperature sensor, an oxygen sensor, and a pH sensor.

13. The kit of claim 11, wherein the sensor is an implantable pressure sensor.

14. The kit of claim 13, wherein the implantable pressure sensor is capable of determining an intra-ventricular pressure.

15. The kit of claim 14, wherein the temperature indicator includes microencapsulated liquid crystal technology.

16. The kit of claim 15, wherein the temperature indicator can change from a first color to a second color in response to a temperature change of about 0.5° C.

17. The kit of claim 15, wherein the temperature indicator can change from a first color to a second color in response to a temperature change in the range of about 0.5° C. to about 2.0° C.

18. The kit of claim 15, wherein the temperature indicator includes an adhesive layer capable of securing the temperature indicator at a desired position adjacent the medical device.

* * * * *